US009585565B2

(12) United States Patent
Carnes

(10) Patent No.: US 9,585,565 B2
(45) Date of Patent: Mar. 7, 2017

(54) SYSTEM, METHOD, AND SOFTWARE FOR AUTOMATING PHYSIOLOGIC DISPLAYS AND ALERTS WITH TRENDING HEURISTICS

(71) Applicant: Tony C. Carnes, Gainesville, FL (US)

(72) Inventor: Tony C. Carnes, Gainesville, FL (US)

(73) Assignee: Covidien LP, Mansfield, MA (US)

( * ) Notice: Subject to any disclaimer, the term of this patent is extended or adjusted under 35 U.S.C. 154(b) by 388 days.

(21) Appl. No.: 13/624,665

(22) Filed: Sep. 21, 2012

(65) Prior Publication Data
US 2014/0085080 A1 Mar. 27, 2014

(51) Int. Cl.
G08B 1/08 (2006.01)
G08B 23/00 (2006.01)
A61B 5/00 (2006.01)

(52) U.S. Cl.
CPC ............ A61B 5/0022 (2013.01); A61B 5/002 (2013.01); A61B 5/746 (2013.01)

(58) Field of Classification Search
CPC ........................................................ G08B 1/08
USPC ..................................................... 340/539.12
See application file for complete search history.

(56) References Cited

U.S. PATENT DOCUMENTS

| 6,193,654 B1* | 2/2001 | Richardson ........ A61B 5/02055 600/300 |
| 2007/0156450 A1 | 7/2007 | Roehm et al. |
| 2010/0179394 A1 | 7/2010 | Sohn et al. |
| 2011/0140896 A1* | 6/2011 | Menzel ............. A61B 5/02055 340/573.1 |

FOREIGN PATENT DOCUMENTS

| WO | 2004/017831 A1 | 3/2004 |
| WO | 2008/002525 A2 | 1/2008 |
| WO | 2009/132434 A1 | 11/2009 |

* cited by examiner

Primary Examiner — Jennifer Mehmood
Assistant Examiner — John Mortell
(74) Attorney, Agent, or Firm — Carter, DeLuca, Farrell & Schmidt, LLP

(57) ABSTRACT

A method for automating physiologic alerts and derived parameters with trending heuristics includes receiving at a mobile patient monitor interface, a first input expression indicative of a first parameter source for first patient parameters from a first medical device from a user. The method further includes receiving, at the mobile patient monitor interface, a second input expression indicative of a second parameter source for second patient parameters from a second medical device from a user. The method further includes applying, at the mobile patient monitor interface, a smoothing operator to the first input expression and the second input expression. The method further includes evaluating, at the mobile patient monitor interface, a complex expression of the first patient parameters and the second patient parameters based on the smoothing operator to initiate display of at least one parameter, derived parameter, trend, or alert on a remote device.

12 Claims, 3 Drawing Sheets

SYSTEM, METHOD, AND SOFTWARE FOR AUTOMATING PHYSIOLOGIC DISPLAYS AND ALERTS WITH TRENDING HEURISTICS

TECHNICAL FIELD

The present disclosure relates generally to alert management, and more particularly to a system, method, and software for automating complex alerts and for smoothing the trend of physiologic values.

BACKGROUND

Patient monitoring systems include alert systems. For example, alert systems may identify simple alert conditions such as a blood pressure exceeding a certain threshold. Proprietary systems include interfaces to display alerts. Proprietary clinical decision support systems include displays of physiologic parameters.

SUMMARY

According to the present disclosure, disadvantages and problems associated with previous techniques for alert management may be reduced or eliminated.

In certain embodiments, a method for automating physiologic alerts with trending heuristics includes receiving at a mobile patient monitor interface, a first input expression from a user indicative of a first parameter source for first patient parameters from a first medical device. The method further includes receiving, at the mobile patient monitor interface, a second input expression from a user indicative of a second parameter source for second patient parameters from a second medical device. The method further includes applying, at the mobile patient monitor interface, a smoothing operator to the first input expression and the second input expression. The method further includes evaluating, at the mobile patient monitor interface, a complex expression of the first patient parameters and the second patient parameters based on the smoothing operator to initiate display of at least one parameter, derived parameter, trended parameter, or alert on a remote device.

Certain embodiments of the present disclosure may provide one or more technical advantages. In conventional systems, more than one of the same or similar medical device can be connected to a patient. Certain parameters may be combined to indicate a "real" change in patient condition. One example is Respiration Rate>16 and O2 Saturation<80. While combining threshold alarms may trigger more intelligent alarms, an improved alerting scenario can be achieved by smoothing the curve of the parameters before evaluating the trigger condition. Devices may perform this calculation by averaging the latest data point with the previous X calculated values before displaying or outputting the value. With automated data capture, the nursing logic that is traditionally used to record a "good" physiologic value may not be present so that artificially high or low values can be captured by the system. If using simple threshold alarms, these artificially out of range values can errantly trigger an alert.

In certain embodiments of the disclosure, a mobile patient monitor interface is provided that addresses these challenges and provides end users an ability to select from a number of aggregate functions and time iterations and apply a smoothing operator to create a customized trigger for their specific needs. Thus, at least one advantage of the present disclosure is that it allows an end user to define a display, trend, derived parameter, or alert with the benefit of trending heuristics and a retrospective look at previously captured data.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

For a more complete understanding of the present disclosure and its features and advantages, reference is now made to the following description, taken in conjunction with the accompanying drawings, in which.

DESCRIPTION OF EXAMPLE EMBODIMENTS

Figure 1:
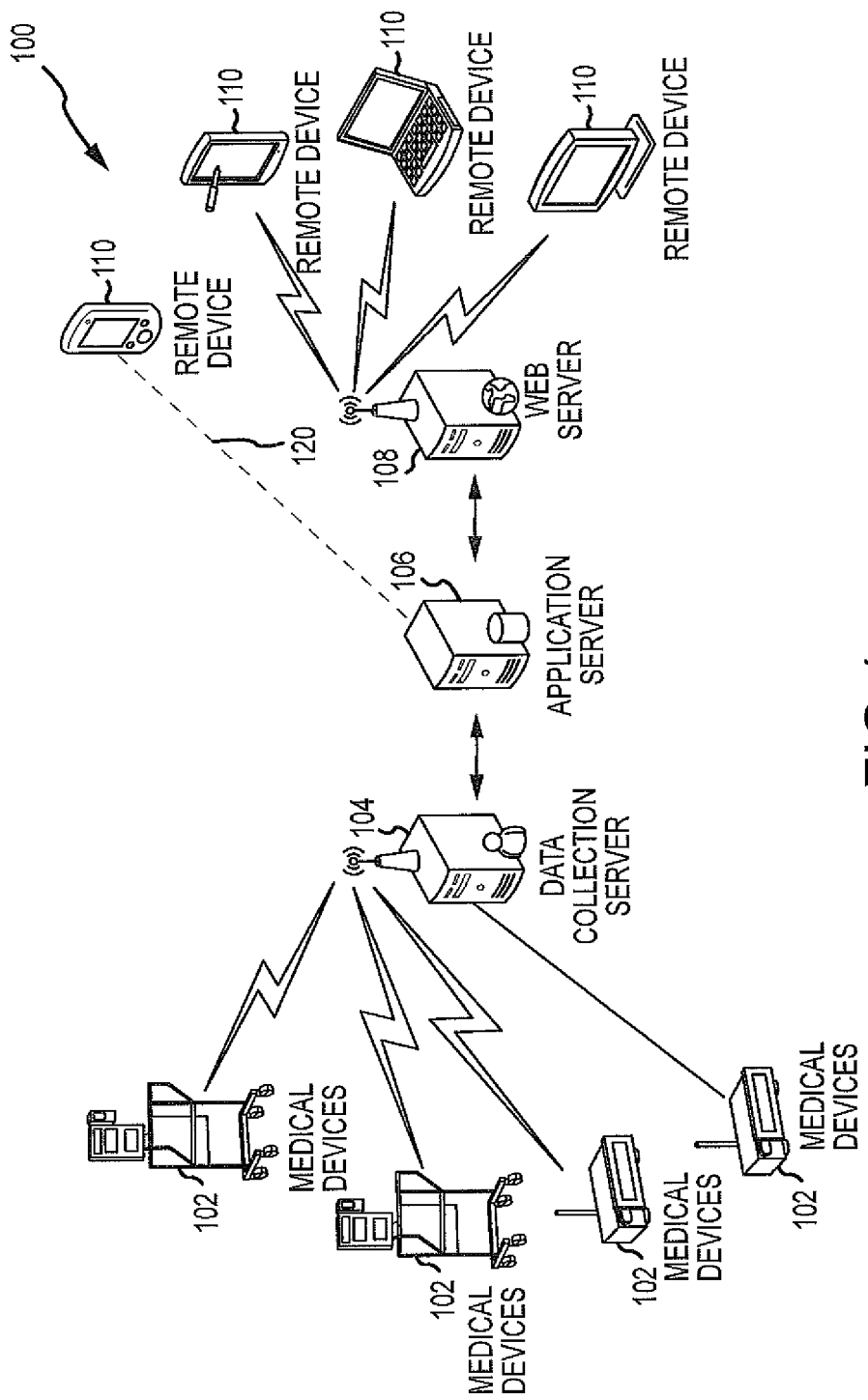
FIG. 1 illustrates an example system for automating complex alerts, according to certain embodiments of the present disclosure.

FIG. 1 illustrates an example system 100 for controlling alert notifications, according to certain embodiments of the present disclosure. System 100 includes one or more medical devices 102, a data collection server 104, an application server 106, a web server 108, and one or more remote devices 110. According to one embodiment, system 100 is operable to monitor medical devices 102 and transform patient parameters into display parameters. In certain embodiments, medical devices 102 generate patient parameters or store patient parameters input by a user, such as a clinician. Patient parameters may refer to any patient identifiers, medical history, clinician notes, alarm thresholds, alarm events, device settings, measurements of values indicating physiological conditions such as oxygen saturation levels, pulse rates, heart rates, other vital signs, and any other output data from medical devices 102. Each medical device 102 may be connected to data collection server 104, which stores the patient parameters in a database. Application server 106 retrieves the patient parameters from the database and processes the patient parameters into display parameters for web server 108. Remote devices 110 request and receive the display parameters and display the display parameters through a browser, thereby enabling clinicians using the remote devices 110 to view the display parameters in remote locations. As described in more detail below, a mobile patient monitor interface at data collection server 104 includes logic that may receive and analyze patient parameters in the form of notifications received from different medical devices 102.

Although this particular implementation of system 100 is illustrated and primarily described, the present disclosure contemplates any suitable implementation of system 100 according to particular needs. For example, although this implementation of the mobile patient monitor interface is illustrated with remote devices 110 that may be using a web interface or a client/server interface, this disclosure contemplates any suitable implementation of the mobile patient monitor interface. In addition, a component of system 100 may include any suitable arrangement of elements, for example, an interface, logic, memory, other suitable element, or a combination of any of the preceding. An interface receives input, sends output, processes the input and/or output, performs other suitable operation, or performs a combination of any of the preceding. An interface may comprise hardware and/or software.

System 100 may include one or more medical devices 102. Medical devices 102 may be any devices that are used for tracking or treating patients. For example, medical devices 102 may include a ventilator connected to a patient to deliver respiratory therapy. As another example, medical devices 102 may include a pulse oximeter that monitors the oxygen saturation of a patient's blood. As another example, medical devices 102 may include a device for tracking a patient without monitoring physiological conditions. In short, medical devices 102 may include any suitable combination of software, firmware, and hardware used to support any medical function. It should be noted that any suitable number of medical devices 102 may be included in system 100. In addition, there may be multiple groups of medical devices 102 in system 100.

According to one embodiment, in addition to performing a medical function, medical devices 102 may generate output data tracked by medical devices 102. For example, the ventilator may generate entries indicating the average volume of air expelled in each breath. The ventilator may generate entries including the parameter settings used by the ventilator and an identification of whether any alarms have been triggered. The ventilator may store the generated entries in local memory and output the entries. In some embodiments, medical devices 102 may generate output data that is related to tracking patient identifications or locations, without necessarily generating data related to a physiological condition. In certain embodiments, medical devices 102 may output data in response to a data request. In certain other embodiments, medical devices 102 may constantly stream output data.

Medical devices 102 may be communicatively coupled to data collection server 104 via a network, according to one embodiment. The network facilitates wireless or wireline communication. The network may communicate, for example, IP packets, Frame Relay frames, Asynchronous Transfer Mode (ATM) cells, voice, video, data, and other suitable information between network addresses. The network may include one or more Serial Networks, local area networks (LANs), radio access networks (RANs), metropolitan area networks (MANS), wide area networks (WANs), all or a portion of the global computer network known as the Internet, and/or any other communication system or systems at one or more locations. In certain embodiments, medical devices may be communicatively coupled to other suitable devices including data collection server 104, application server 106, web server 108, and remote devices 110.

System 100 may include one or more data collection servers 104, referred to primarily in the singular throughout this disclosure. Data collection server 104 may include one or more electronic computing devices operable to receive, transmit, process, and store data associated with system 100. For example, data collection server 104 may include one or more general-purpose PCs, Macintoshes, workstations, Unix-based computers, server computers, one or more server pools, or any other suitable devices. In certain embodiments, data collection server 104 includes a web server. In short, data collection server 104 may include any suitable combination of software, firmware, and hardware. Although a single data collection server 104 is illustrated, the present disclosure contemplates system 100 including any suitable number of data collection servers 104. Moreover, although referred to as a data collection server, the present disclosure contemplates data collection server 104 comprising any suitable type of processing device or devices.

According to one embodiment, data collection server 104 receives patient parameters from medical devices 102. For example, data collection server 104 may request patient parameters from a medical device 102 and receives patient parameter sets from the medical device 102 in response to the request. As another example, data collection server 104 may receive streamed output data from a medical device 102. As another example, data collection server 104 may be configured to periodically request new data from medical device 102. Data collection server 104 may map the received patient parameters to match internal fields in the database and then transmit the data to a database, according to one embodiment. The stored data may be accessed by application server 106. According to one embodiment of the disclosure, data collection server may receive notifications in the form of patient parameters and transmit triggered notifications.

System 100 may include one or more application servers 106, referred to primarily in the singular throughout this disclosure. Application server 106 may include one or more electronic computing devices operable to receive, transmit, process, and store data associated with system 100. For example, application server 106 may include one or more general-purpose PCs, Macintoshes, workstations, Unix-based computers, server computers, one or more server pools, or any other suitable devices. In short, application server 106 may include any suitable combination of software, firmware, and hardware. Although a single application server 106 is illustrated, the present disclosure contemplates system 100 including any suitable number of application servers 106. Moreover, although referred to as an application server, the present disclosure contemplates application server 106 comprising any suitable type of processing device or devices.

According to one embodiment, application server 106 creates a data service that runs on a conventional web services platform for transmitting data to web server 108. For example, application server 106 may create webpage data using the patient parameters, and that webpage data is transmitted to web server 108 for display. Application server 106 may maintain an activity log that logs data requests from remote devices 110 to track certain activities performed at the remote devices 110. Application server 106 may create additional data that causes a pop-up window to appear on the mobile device when any of the changed patient parameters are selected. That window may list all of the changed patient parameters and provides a single button through which a user may indicate that that the changed patient parameters have been viewed. If that button is activated, the mobile device may transmit a message to application server 106 and application server 106 may then unflag those patient parameters, such that the depiction of those patient parameters on remote device 110 may return to the original color. In certain embodiments, application server 106 may transmit data directly to remote devices 110.

System 100 may include one or more web servers 108, referred to primarily in the singular throughout this disclosure. Web server 108 may include one or more electronic computing devices operable to receive, transmit, process, and store data associated with system 100. For example, web server 108 may include one or more general-purpose PCs, Macintoshes, workstations, Unix-based computers, server computers, one or more server pools, or any other suitable devices. In short, web server 108 may include any suitable combination of software, firmware, and hardware. Although a single web server 108 is illustrated, the present disclosure contemplates system 100 including any suitable number of web servers 108. Moreover, although referred to as a web server, the present disclosure contemplates web server 108 comprising any suitable type of processing device or devices.

According to one embodiment, web server 108 creates a data service that runs on a conventional web services platform for receiving data from application server 106 and transmitting data to remote devices 110. For example, web server 108 may receive webpage data from application server 106 and transmit, upon request in certain embodiments, to remote devices 110.

System 100 may include one or more remote devices 110. Remote devices 110 may be any device that provides output to and can receive input from a user, such as a clinician. Each remote device 110 may include one or more computer systems at one or more locations. A remote device 110 may connect to web server 108 or directly to application server 106 as indicated by reference number 120. Each computer system may include any appropriate input devices (such as a keypad, touch screen, mouse, or other device that can accept input), output devices, mass storage media, or other suitable components for receiving, processing, storing, and communicating data. Both the input device and output device may include fixed or removable storage media such as a magnetic computer disk, CD-ROM, or other suitable media to both receive input from and provide output to a user. Each computer system may include a personal computer, workstation, network computer, kiosk, wireless data port, personal data assistant (PDA), one or more processors within these or other devices, or any other suitable processing device.

According to one embodiment, remote devices 110 display one or more web pages hosted by application server 106 and/or web server 108 with patient parameters from medical devices 102. For example, a clinician may activate a browser on remote device 110 and navigate to the web page hosted by web server 108. The browser may render the web page, which includes patient parameters generated by medical devices 102. The web page may provide a summary of all the medical devices 102 under a clinician's responsibility. In addition, the web may display a detailed view that displays specific device data, therapy parameter data, and alarm status data.

Although FIG. 1 depicts separate devices for data collection server 104, application server 106, and web server 108, it will be readily apparent that the functions of these devices may be combined into a single device that receives patient parameters from medical devices 102 and transforms the patient parameters into display parameters. It will also be understood that this single device may alternatively transmit the display parameters to remote device 110. In certain embodiments, data collection server 104 may be a bedside device that receives patient parameters from medical devices 102.

It will also be understood that the functions may be allocated differently than shown, with application server 106 additionally performing the functions of web server 108 or the functions of data collection server 104. In another embodiment, a single device may receive patient parameters, transform those patient parameters into display parameters, and display the display parameters on a screen.

A user of system 100 may detect patient conditions by examining a combination of patient parameters received from a number of medical devices 102. After the patient parameters are captured, parsed, and semantically mapped, there are a substantial number of possible uses of the data. The patient parameters may be displayed, trended, used to calculate derived parameters, used in smart alarms and alerts, and even mined for content. An issue arises, however, when the same logical value can come from multiple sources. For example, the same or similar patient parameters can come from multiple sources and all of the values may be manually entered. In addition, for certain types of medical devices 102, more than one of the same or similar medical device can be connected to a patient. Given a multitude of sources for a given parameter, such as heart rate, there are several considerations that present physiologic alert systems do not consider, such as: (1) how does one determine which heart rate to put on a graph, display in tabular format, or include in a complex alert detection algorithm; (2) which source of heart rate is the correct one; and (3) what if the selected type of device is not connected for the given patient?

In certain embodiments of the disclosure, system 100 may include a mobile patient monitor interface to address these concerns. The mobile patient monitor interface may refer to any suitable hardware and/or software operable to be configured to: receive at least a first input expression indicative of a first parameter source for first patient parameters from a first medical device from a user; receive a second input expression indicative of a second parameter source for second patient parameters from a second medical device from a user; apply, at the mobile patient monitor interface, a smoothing operator to the first input expression and the second input expression; and evaluate a complex expression of the first patient parameters and the second patient parameters based on the smoothing operator to initiate display of at least one parameter, derived parameter, trended parameter, or alert on a remote device. Therefore, the mobile patient monitor interface provides end users the ability to select from a number of aggregate functions and time iterations and apply a smoothing operator to create a customized trigger or display parameter for their specific needs. Additional details of example embodiments of the mobile patient monitor interface are discussed below with reference to FIGS. 2-3.

Figure 2:
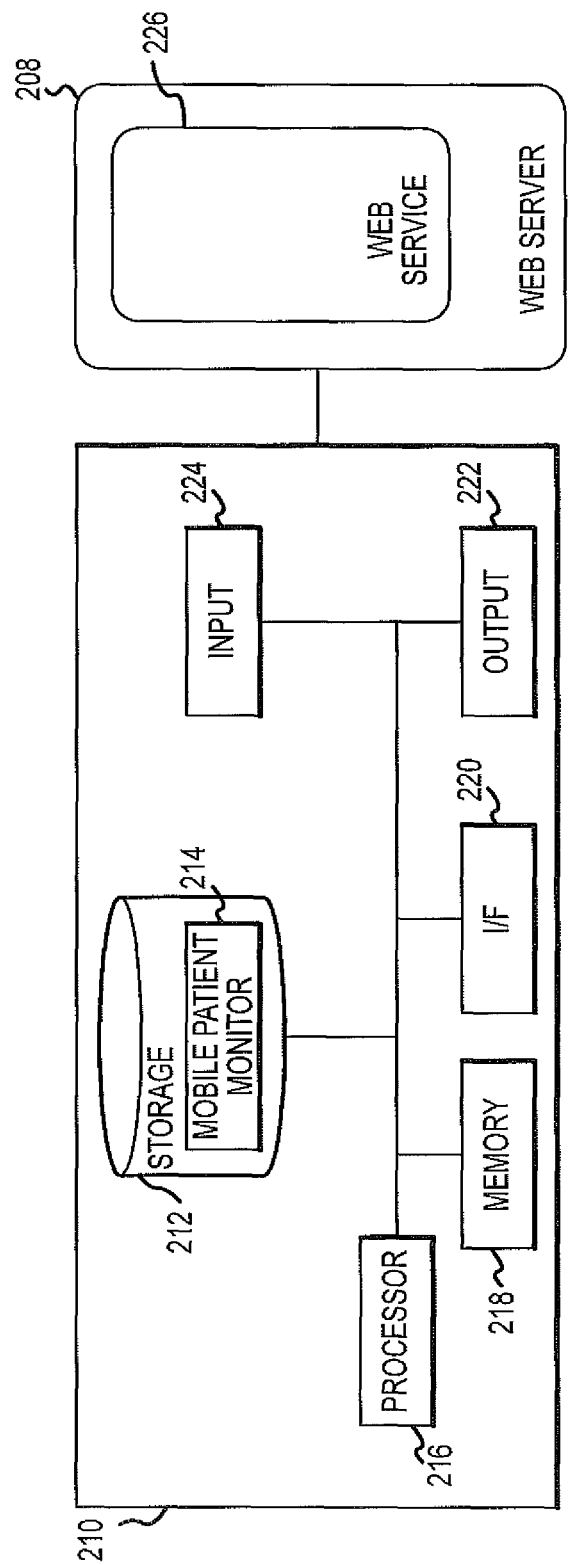
FIG. 2 illustrates an example remote device of the system for patient monitoring of FIG. 1, according to certain embodiments of the present disclosure.

FIG. 2 illustrates an example remote device 210 of the system 100 for patient monitoring in FIG. 1, according to certain embodiments of the present disclosure. Remote device 210 may be substantially similar to remote device 110 of FIG. 1. In FIG. 2, a remote device 210 is shown as a mobile telephone communicatively coupled with a web server 208 having a web service 226 capability. Web server 208 may be substantially similar to web server 108 of FIG. 1. Remote device 210 includes a storage device 212, a mobile patient monitor interface 214, a processor 216, a memory 218, a communication interface (I/F) 220, an output device 222, and an input device 224, which are discussed in further detail below. Although this particular implementation of remote device 210 is illustrated and primarily described, the present disclosure contemplates any suitable implementation of remote device 210 according to particular needs.

Storage device 212 may include any suitable device operable for storing data and instructions. Storage device 212 may include, for example, a magnetic disk, flash memory, optical disk, or other suitable data storage device.

Mobile patient monitor interface 214 may include any suitable logic embodied in computer-readable media, and when executed, that is operable to be configured to: receive at least a first input expression indicative of a first parameter source for first patient parameters from a first medical device from a user; receive a second input expression indicative of a second parameter source for second patient parameters from a second medical device from a user; apply, at the mobile patient monitor interface, a smoothing operator to the first input expression and the second input expression; and evaluate a complex expression of the first patient parameters and the second patient parameters based on the smoothing operator to initiate display of at least one parameter, derived parameter, trended parameter, or alert on a remote device.

Thus, according to certain embodiments of the present disclosure, mobile patient monitor interface 214 provides end users the ability to select from a number of aggregate functions and time iterations and apply a smoothing operator to create a customized trigger for their specific needs. For example, the algorithm may include a smoothing operator may be on parameter, the parameter, time basis of smoothing operator, time differential for comparing prior and current condition, smoothing operator for end parameter, end parameter, time basis of second parameter smoothing operator, comparison operator, and constants. Smoothing operators include, but are not limited to an exact operation, an averaging operation, a median operation, a min operation (e.g., an operation to identify the smallest value from the numbers provided), a max operation (e.g., an operation to identify the largest value from the numbers provided), and a count operation (e.g. an operation to identify the count of the numbers provided). The time basis may be current time, or it can reference previous×seconds, minutes, hours, or days. For example, mobile patient monitor interface 214 may be extended to allow for a smoothing effect on an example complex expression (Respiration Rate>16 and O2 Saturation<80) as follows:

Avg(Respiration Rate values captured in last 1 minute)>16 and Avg($O2$ Saturation values captured in last 30 seconds)<80

As another example, to determine if a value is truly changing by a certain percentage (e.g., X %), up or down, over time, mobile patient monitor interface 214 may allow for a differential time comparison to be added for the parameters in question. That is, mobile patient monitor interface 214 may be used to create the following complex expression:

Exact(Respiration Rate from 1 hour ago)−Exact(Respiration Rate from right now)/Exact(Respiration Rate from 1 hour ago)>0.1

While this complex expression may yield an accurate value for percent change over time, it is subject to artificially triggering if the patient were moving during data capture. Therefore, in certain embodiments, mobile patient monitor interface 214 may be used to create a more robust complex expression for determining if Respiration Rate has fallen by 10% in the past hour, such as:

Avg(Respiration Rate starting 1 hour ago for 1 minute)−Avg(Respiration Rate in last 1 minute)/Avg(Respiration Rate starting 1 hour ago for 1 minute)>0.1

Additional details of mobile patient monitor interface 214 are provided below with reference to FIG. 3.

Processor 216 may include any suitable device operable to execute instructions and manipulate data to perform operations for mobile patient monitor interface 214. Processor 216 may include, for example, any type of central processing unit (CPU).

Memory 218 may include any computer memory (for example, Random Access Memory (RAM) or Read Only Memory (ROM), mass storage media (for example, a hard disk), removable storage media (for example, a Compact Disk (CD) or a Digital Video Disk (DVD)), database and/or network storage (for example, a server). Memory 218 may comprise any other computer-readable tangible medium, or a combination of any of the preceding.

I/F 220 may include any suitable device operable to receive input for mobile patient monitor interface 214, send output from mobile patient monitor interface 214, perform suitable processing of the input or output or both, communicate to other devices, or any combination of the preceding. I/F 220 may include appropriate hardware (for example, a modem, network interface card, etc.) and software, including protocol conversion and data processing capabilities, to communicate through a Serial Network, LAN, WAN, or other communication system that allows mobile patient monitor interface 214 to communicate to other devices. I/F 220 may include one or more ports, conversion software, or a combination of any of the preceding.

Output device 222 may include any suitable device operable for displaying information to a user. Output device 222 may include, for example, a video display, a printer, a plotter, or other suitable output device. In certain embodiments, output device 222 may reformat data in any suitable format to be transmitted to other systems.

Input device 224 may include any suitable device operable to input, select, and/or manipulate various data and information. Input device 224 may include, for example, a keyboard, mouse, graphics tablet, joystick, light pen, microphone, scanner, or other suitable input device.

Modifications, additions, or omissions may be made to remote device 210 without departing from the scope of the disclosure. The components of remote device 210 may be integrated or separated. Moreover, the operations of remote device 210 may be performed by more, fewer, or other components. For example, although mobile patient monitor interface 214 is displayed as part of storage device 212, mobile patient monitor interface 214 may be stored in any suitable location, including in another suitable device shown in FIG. 1, and the operations of mobile patient monitor interface 214 may be performed by more than one component. Additionally, operations of remote device 210 may be performed using any suitable logic. As used in this document, "each" refers to each member of a set or each member of a subset of a set. Further details of an example remote device 210 and the operations of mobile patient monitor interface 214 are provided below with reference to FIG. 3.

Figure 3:
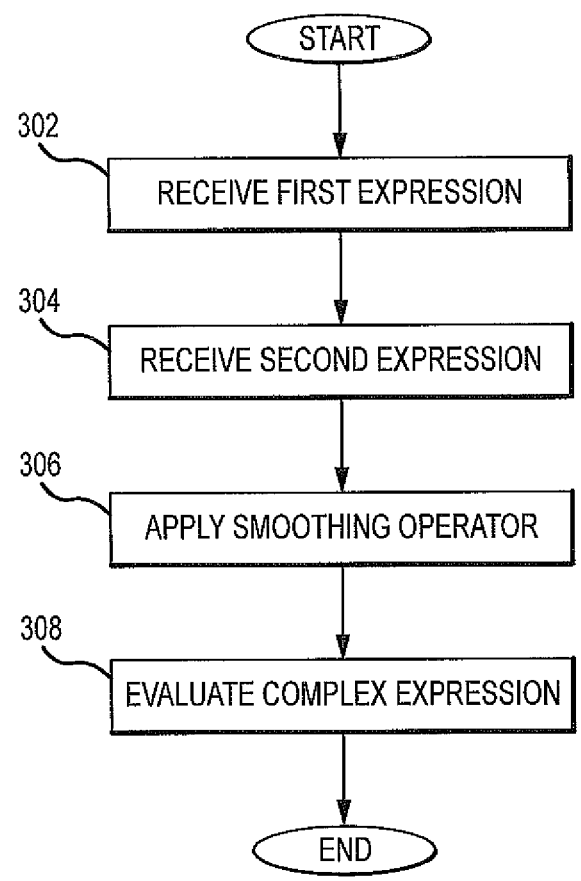
FIG. 3 illustrates an example method for automating physiologic alerts with trending heuristics, according to certain embodiments of the present disclosure.

FIG. 3 illustrates an example method for automating physiologic alerts with trending heuristics, according to certain embodiments of the present disclosure. The method begins at step 302 where a first input expression is received that is indicative of a first parameter source for first patient parameters from a first medical device from a user. At step 304, a second input expression is received that is indicative of a second parameter source for second patient parameters from a second medical device from a user. At step 306, a smoothing operator is applied to the first input expression and the second input expression. At step 308, a complex expression of the first plurality of patient parameters and the second plurality of patient parameters is evaluated based on the smoothing operator to initiate display of at least one alert on a remote device. It should be understood that some of the steps illustrated in FIG. 3 may be combined, modified or deleted where appropriate, and additional steps may be added to the flowchart. Additionally, as indicated above, steps may be performed in any suitable order without departing from the scope of the disclosure.

Although the present disclosure has been described with several embodiments, diverse changes, substitutions, variations, alterations, and modifications may be suggested to one skilled in the art, and it is intended that the disclosure encompass all such changes, substitutions, variations, alterations, and modifications as fall within the spirit and scope of the appended claims.

What is claimed is:

1. A method for automating physiologic alerts and derived parameters with trending heuristics, comprising:
   receiving, at a mobile patient monitor interface, a first input expression indicative of a first parameter source for a first plurality of patient parameters from a first medical device from a user;
   receiving, at the mobile patient monitor interface, a second input expression indicative of a second parameter source for a second plurality of patient parameters from a second medical device from a user;
   applying, at the mobile patient monitor interface, a smoothing operator to the first input expression and the second input expression, wherein the smoothing operator applied to the first input expression includes a time basis in which a first average of the first plurality of patient parameters is taken over a first time period, a second average of the first plurality of patient parameters is taken over a second time period more current than the first time period, the first average of the first plurality of patient parameters is subtracted from the second average of the first plurality of patient parameters to yield a value, and the value is divided by the first average of the first plurality of patient parameters; and
   evaluating, at the mobile patient monitor interface, a complex expression of the first plurality of patient parameters and the second plurality of patient parameters based on the smoothing operator to initiate display of at least one alert or derived parameter on a remote device.

2. A system for automating physiologic alerts and derived parameters with trending heuristics, comprising:
   one or more processing units operable to:
      receive at a mobile patient monitor interface, a first input expression indicative of a first parameter source for a first plurality of patient parameters from a first medical device from a user;
      receive at the mobile patient monitor interface, a second input expression indicative of a second parameter source for a second plurality of patient parameters from a second medical device from a user;
      apply, at the mobile patient monitor interface, a smoothing operator to the first input expression and the second input expression, wherein the smoothing operator applied to the first input expression includes a time basis in which a first average of the first plurality of patient parameters is taken over a first time period, a second average of the first plurality of patient parameters is taken over a second time period more current than the first time period, the first average of the first plurality of patient parameters is subtracted from the second average of the first plurality of patient parameters to yield a value, and the value is divided by the first average of the first plurality of patient parameters; and
      evaluate at the mobile patient monitor interface, a complex expression of the first plurality of patient parameters and the second plurality of patient parameters based on the smoothing operator to initiate display of at least one alert or derived parameter on a remote device.

3. A non-transitory computer-readable medium storing a computer program product that, when executed, is operable to:
   receive at a mobile patient monitor interface, a first input expression indicative of a first parameter source for a first plurality of patient parameters from a first medical device from a user;
   receive at the mobile patient monitor interface, a second input expression indicative of a second parameter source for a second plurality of patient parameters from a second medical device from a user;
   apply, at the mobile patient monitor interface, a smoothing operator to the first input expression and the second input expression, wherein the smoothing operator applied to the first input expression includes a time basis in which a first average of the first plurality of patient parameters is taken over a first time period, a second average of the first plurality of patient parameters is taken over a second time period more current than the first time period, the first average of the first plurality of patient parameters is subtracted from the second average of the first plurality of patient parameters to yield a value, and the value is divided by the first average of the first plurality of patient parameters; and
   evaluate at the mobile patient monitor interface, a complex expression of the first plurality of patient parameters and the second plurality of patient parameters based on the smoothing operator to initiate display of at least one alert or derived parameter on a remote device.

4. The method of claim 1, wherein the smoothing operator applied to the second input expression includes a time basis in which a first average of the second plurality of patient parameters is taken over a third time period, a second average of the second plurality of patient parameters is taken over a fourth time period more current than the third time period, the first average of the second plurality of patient parameters is subtracted from the second average of the second plurality of patient parameters to yield a value, and the value is divided by the first average of the second plurality of patient parameters.

5. The method of claim 1, wherein the smoothing operator applied to the second input expression includes a time basis indicating a percentage of change over time.

6. The method of claim 1, further comprising displaying the at least one alert or derived parameter on the remote device, based on the evaluation of the complex expression.

7. The system of claim 2, wherein the smoothing operator applied to the second input expression includes a time basis in which a first average of the second plurality of patient parameters is taken over a third time period, a second average of the second plurality of patient parameters is taken over a fourth time period more current than the third time period, the first average of the second plurality of patient parameters is subtracted from the second average of the second plurality of patient parameters to yield a value, and the value is divided by the first average of the second plurality of patient parameters.

8. The system of claim 2, wherein the smoothing operator applied to the second input expression includes a time basis indicating a percentage of change over time.

9. The system of claim 2, wherein the one or more processing units are operable to further display the at least one alert or derived parameter on the remote device, based on the evaluation of the complex expression.

10. The computer-readable medium of claim 3, wherein the smoothing operator applied to the second input expression includes a time basis in which a first average of the second plurality of patient parameters is taken over a third time period, a second average of the second plurality of patient parameters is taken over a fourth time period more current than the third time period, the first average of the second plurality of patient parameters is subtracted from the second average of the second plurality of patient parameters to yield a value, and the value is divided by the first average of the second plurality of patient parameters.

11. The computer-readable medium of claim 3, wherein the smoothing operator applied to the second input expression includes a time basis indicating a percentage of change over time.

12. The computer-readable medium of claim 3, wherein the computer program product that, when executed, is operable to further display the at least one alert or derived parameter on the remote device, based on the evaluation of the complex expression.

* * * * *